United States Patent
Swoyer et al.

(10) Patent No.: US 6,512,958 B1
(45) Date of Patent: Jan. 28, 2003

(54) PERCUTANEOUS MEDICAL PROBE AND FLEXIBLE GUIDE WIRE

(75) Inventors: John M. Swoyer, Andover, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 42 days.

(21) Appl. No.: 09/846,559

(22) Filed: Apr. 26, 2001

(51) Int. Cl.$^7$ ................................................ A61N 1/05
(52) U.S. Cl. ...................... 607/117; 600/585; 606/129
(58) Field of Search ..................... 607/116, 117; 606/129; 600/373, 377, 393, 585

(56) References Cited

U.S. PATENT DOCUMENTS

| | | | |
|---|---|---|---|
| 3,973,556 A | * 8/1976 | Fleischhacker et al. ...... | 600/585 |
| 4,052,989 A | 10/1977 | Kline | |
| 4,961,433 A | * 10/1990 | Christian ...................... | 600/585 |
| 5,209,735 A | * 5/1993 | Lazarus ........................ | 600/585 |
| 5,255,691 A | * 10/1993 | Otten ........................... | 607/117 |
| 5,275,611 A | * 1/1994 | Behl ............................ | 600/585 |
| 5,728,148 A | * 3/1998 | Bostrom et al. .............. | 600/373 |
| 5,902,331 A | * 5/1999 | Bonner et al. ............... | 600/585 |
| 5,957,965 A | * 9/1999 | Moumane et al. ........... | 607/117 |
| 6,055,456 A | * 4/2000 | Gerber ......................... | 607/117 |
| 6,104,960 A | * 8/2000 | Duysens et al. ............. | 607/117 |
| 6,134,467 A | 10/2000 | Ouchi | |
| 6,162,221 A | 12/2000 | Ouchi | |
| 6,217,527 B1 | * 4/2001 | Selmon et al. .............. | 600/585 |

FOREIGN PATENT DOCUMENTS

| | | |
|---|---|---|
| DE | 4333910 A1 | 4/1995 |
| EP | 0972538 A2 | 1/2000 |

\* cited by examiner

*Primary Examiner*—John Rivell
(74) *Attorney, Agent, or Firm*—Thomas G. Berry; Eric R. Waldkoetter; Thomas F. Woods

(57) ABSTRACT

A medical instrument for obtaining access to a site within the body directly inserted through the skin or through an incision in the skin to enable introduction of further medical instruments to the percutaneously accessed site or from the percutaneously accessed site to a more remote site in the body. The instrument comprises a combined medical probe and flexible guide wire for introduction of the further elongated diagnostic or surgical or therapy delivery devices over the guide wire and probe. The combined medical probe and flexible guide wire further comprises a stiff tissue penetrating probe having a probe length between a probe proximal end and a probe distal end, the probe length shorter than the elongated medical device length, and a flexible guide wire body having a guide wire length between a guide wire body proximal end and a guide wire body distal end, the guide wire distal end coupled to the probe proximal end, the guide wire length sufficiently long to support the elongated medical device to enable its over-the-wire advancement over the guide wire body and probe.

20 Claims, 7 Drawing Sheets

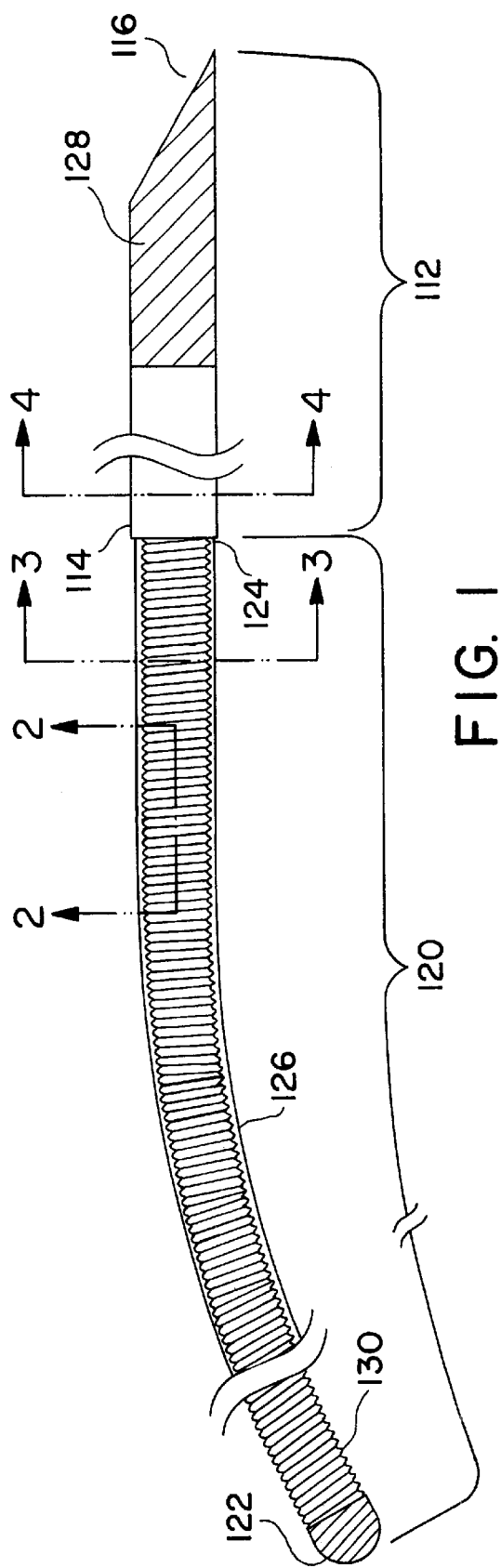
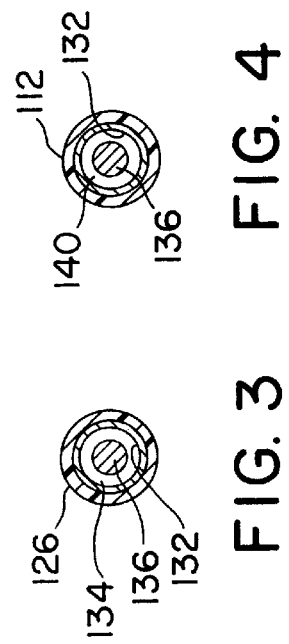
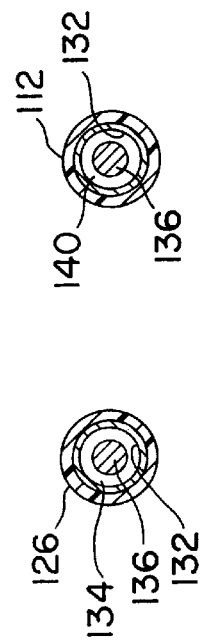
FIG. 1
FIG. 2
FIG. 3
FIG. 4

PERCUTANEOUS MEDICAL PROBE AND FLEXIBLE GUIDE WIRE

BACKGROUND OF THE INVENTION

1. Field of the Invention

This invention relates generally to a medical instrument for obtaining access to a site within the body directly inserted through the skin or through an incision in the skin to enable introduction of further medical instruments to the percutaneously accessed site or from the percutaneously accessed site to a more remote site in the body, and more particularly to a combined medical probe and flexible guide wire (or guidewire) for introduction of the further elongated diagnostic or surgical or therapy delivery devices over the guide wire and probe.

2. Description of Related Art

Numerous medical procedures have come into common usage for accessing a site within the body in a minimally invasive manner that avoids surgical exposure of the site to perform a wide variety of diagnostic and therapeutic procedures involving use of a small diameter probe (defined herein as including a needle, a stiff wire, a trocar or the like). Such medical procedures generally involve use of the probe to create a percutaneous (also referred to in the art as transcutaneous or trans-dermal) pathway through the skin and subcutaneous tissue. The probe is either pushed or stuck directly through the patient's skin or is inserted through a small surgical incision in the skin to a particular percutaneously accessed site of interest or to a starting point of an access pathway to a remote site of interest. Then, the percutaneous pathway is expanded in a variety of ways to enable insertion of larger diameter diagnostic, surgical or therapeutic devices. In the course of such procedures, it is common to advance introducers, dilators, and other tubular instruments over the probe and over one another in a prescribed sequence to enlarge the percutaneous pathway by spreading tissue apart. The probe is removed at a particular point in the procedure depending upon the selection of instruments that are used in the sequence of enlarging the percutaneous pathway.

In one approach, the percutaneous pathway that is finally created is defined by the lumen of a hollow tubular catheter or introducer or the like extending from the skin to the accessed site to enable passage of therapeutic or diagnostic or surgical devices therethrough to the accessed site. In another approach, the percutaneous pathway is defined by the outer guiding surface of a hollow or solid core stylet or guide wire extending from the skin to the accessed site to enable over-the-wire advancement of therapeutic or diagnostic or surgical devices to the percutaneous access site.

When the percutaneously accessed site is the site of interest, a diagnostic, surgical or therapeutic device is introduced through the expanded percutaneous pathway in the through-the-lumen or over-the wire manner to perform a procedure or deliver a therapy to the accessed site.

When a more remote site is the site of interest, the same or a further accessing instrument or tool, e.g. an elongated catheter or cannula or guide wire (or a combination of the same used in a predetermined sequence), is advanced through the percutaneous pathway and from the percutaneously accessed site through a remote access pathway to the remote site of interest. The access pathway may be a vascular pathway from an incision into a vein or artery at the percutaneously accessed site that is employed to introduce cardiac catheters and leads or vascular instruments for diagnostic, therapeutic or surgical procedures at remote sites in the heart or in the vascular system. Or the access pathway may be through or into a body organ or cavity or lumen or other structure to the remote site of interest.

Usually, the percutaneous pathway is relatively straight, but the access pathway twists and turns following the anatomy of the body. Typically, the accessing instrument that is left in place extending to the remote site comprises a flexible guide wire or guide catheter that can bend to follow the access pathway. The flexible guide wire or guide catheter then extends from an accessible proximal end left outside the patient's body through the percutaneous pathway and the access pathway to a distal end advanced to the remote site. Then, a diagnostic or surgical or therapeutic instrument is introduced over-the-wire or through-the-lumen to enable a diagnostic or surgical procedure or to provide a therapy at the remote site.

Many therapeutic and/or diagnostic procedures have been developed that involve obtaining access to a desired percutaneous access site or remote site in the body as described above and the implantation of a temporary or permanent electrical stimulation lead, sensor bearing lead or drug delivery catheter that is coupled with a permanently implanted or external pulse generator and/or monitor or drug delivery device. In many procedures, it is desirable to insert a therapeutic or diagnostic lead or catheter having as small an outside diameter as is possible to locate a distal segment thereof at a desired site while minimally displacing body tissue. The electrical stimulation lead, sensor bearing lead or drug delivery catheter is implanted via such a percutaneous pathway and typically extends through an access pathway to locate electrical sensing and/or stimulation electrodes or sensors or drug delivery outlets at the remote site. In permanent implantation procedures, the proximal ends of such sensor and/or electrode bearing leads or catheters are coupled to implantable pulse generators and/or monitors or drug delivery devices that are implanted subcutaneously near the percutaneous pathway or at a distance from the percutaneous pathway. In the latter case, the lead or catheter is relatively long or is attached to a relatively long lead or catheter body that is implanted through a subcutaneous tunnel to the remote medical device.

For example, access to the epidural space of the spinal column and to introduce a stimulation lead into the epidural space is disclosed in commonly assigned U.S. Pat. No. 5,255,691. An epidural needle assembly is employed to reach a percutaneously accessed site in the epidural space, and a stylet stiffened stimulation lead is introduced through the needle lumen and advanced past the percutaneously accessed site through an access pathway in the epidural space to position the lead electrodes at a remote site still within the epidural space. The needle and stylet are withdrawn, and the lead connector elements are connected with an implantable neurostimulator that is implanted subcutaneously in the body.

As noted above, the initial step in forming a percutaneous pathway typically involves use of a probe, such as a stiff, sharp tip or blunt tip, straight needle, that is advanced by a clinician from the skin or skin incision to the percutaneously accessed site. In most cases, the probe is aimed in a carefully determined direction from the skin to the site so that the distal tip of the needle reaches the site of interest with the needle axially aligned to body feature that must be accessed. For example, percutaneous pathways are formed to allow miniaturized neurostimulation leads to be advanced into the spinal column as disclosed, for example, in the above-referenced '691 patent, or through a foramen of the sacrum (as disclosed, for example, in commonly assigned U.S. Pat. Nos. 5,957,965, 6,104,960 and 6,055,456) in carefully determined and particularly sensitive directions.

The direction of advancement of the needle or other probe in three-dimensional space is determined in advance by use of radiographic imaging or palpation of tissue or stealth station technology. The probe is then carefully held and advanced from the skin so that it is axially aligned with the predetermined direction. This procedure is most easily accomplished using a probe that is no longer than necessary to extend from the skin to the percutaneously accessed site. It is easier to accurately aim and advance a short probe than a long probe that extends away from the skin. The probe is necessarily small in diameter and stiff, and such a probe tends to flex and bend in direct relation to its length. Thus, a long probe can bend as it is advanced and depart from the intended direction. Moreover, the probe becomes more difficult to aim and hold to a desired direction as its length increases, because slight deviations from the intended direction are magnified through the length of the probe.

Therefore, relatively short probes are employed having a shorter exposed length extending from the skin than the length of a lead or catheter or instrument that is to be advanced through the percutaneous pathway. Typically, the probe length is shorter than the overall length of the lead or catheter which usually includes a proximal segment that is to be extended to an external or implanted device located or implanted at a distance from the percutaneous pathway. Thus, it is not possible to grasp the proximal end of the probe if an attempt is made to advance any such lead or catheter or instrument over the probe to maintain the carefully determined direction of insertion of the probe.

We have found that it would be desirable to be able to employ the probe itself to guide longer dilators or surgical instruments or leads or catheters or the like in an over-the-wire manner to a remote site or just to the percutaneous access site to minimize the number of instruments used and steps in the procedure.

SUMMARY OF THE INVENTION

Accordingly, the present invention recognizes and provides a solution to the problems associated with defining a percutaneous pathway for over-the-wire advancement of a therapeutic or diagnostic instrument or a pathway expanding instrument.

In accordance with a preferred embodiment of the invention, a combined percutaneous medical probe and guide wire is employed to form a percutaneous pathway to a percutaneously accessed site and enables over-the-wire advancement of an elongated medical device to the percutaneously accessed site and into an access pathway. The combined medical probe eliminates the need to introduce a separate guide wire to the percutaneously accessed site.

The combined percutaneous medical probe and guidewire comprises a stiff tissue penetrating probe having a first length adapted to provide the percutaneous pathway to the percutaneously accessed site of interest. The tissue penetrating probe is coupled with a flexible guide wire body that remains entirely or substantially outside the body having a second length sufficiently long to support the full length of the elongated medical device to enable its over-the-wire advancement. The tissue penetrating probe is adapted to be manually grasped, aligned axially in a predetermined direction, and advanced from the skin to the percutaneously accessed site while the flexible guide wire droops away from the attachment with the proximal end of the probe. Thus, the relatively short probe is more readily and accurately aligned to the predetermined direction to facilitate accurate advancement. Then, a further instrument, e.g. a dilator having a through-lumen, can be advanced over the flexible guide wire body and distally over the probe to dilate the tissue surrounding it if necessary. An elongated medical device having a through-lumen comprising one of a lead or a catheter or a surgical instrument can be inserted over the combined flexible guide wire body and the probe to locate a distal end thereof at the percutaneously accessed site or through the percutaneously accessed site to a remote site in the body.

The percutaneously accessed site is typically within a vessel or organ lumen or within the brain or within a body cavity that is reached by the distal end of the probe that is passed through the skin and subcutaneous tissue. The combined medical probe can be employed as a test stimulation or electrical sensing lead to apply electrical stimulation to responsive tissue, e.g., muscle or nerve fibers or brain cells, or to receive electrical signals from tissue at the percutaneously accessed site. The probe is preferably formed of conductive metal and electrically insulated along its length except for a stimulation or sense electrode area at or adjoining the probe distal tip. The flexible guide wire is preferably formed of an electrical conductor that is electrically insulated along its length except for a proximal electrode connector element.

Preferably, the probe is formed of a needle with a closed distal tip to prevent coring of tissue. The flexible guide wire body is preferably formed of a coiled wire within an insulating sheath having a guide wire body diameter about equal with the diameter of the needle. An inextensible core wire is fixed to and extends from the exposed proximal end of the coiled wire through the coiled wire lumen and the needle lumen to the beveled needle distal tip and thereby inhibits stretching of the guide wire body and coring of tissue by the needles distal tip. Alternatively, the core wire can be affixed more proximally within the needle lumen or otherwise fixed to the needle proximal end, and the needle lumen can be filled with a further wire or filler material to provide an equivalent structure. The continuous core wire provides a continuous electrical conductor that is relatively noise free when the combined medical probe and guide wire is used as a stimulation or electrical sensing lead.

One preferred use of the combined percutaneous medical probe and guide wire is to form a percutaneous pathway to a sacral nerve that can be accessed in a posterior approach through a foramen of the patient's sacrum where the sacral nerve extends anteriorly and inferiorly so as to place an implantable neurostimulation lead electrode in operative relation with the sacral nerve. In this procedure, it is important to accurately insert the probe tip into the foramen at a prescribed angle to access the sacral nerve without damaging it. The sacral nerve response to applied electrical test stimulation can be assessed at differing depths of insertion of the exposed distal tip electrode to map the optimal location of the lead electrode.

If necessary, dilation of tissue around the probe can be undertaken. A dilator can be advanced over the guide wire body until the guide wire proximal end is exposed from the dilator lumen at the lead body proximal end. The guide wire body can be straightened to enable advancement of the dilator over the probe and withdrawal of the dilator.

A neurostimulation lead can be advanced over the guide wire body until the guide wire proximal end is exposed from the lead body lumen at the lead body proximal end.

The guide wire body can be straightened to enable advancement of the lead over the probe until the neurostimulation lead electrode(s) is optimally advanced into operative relation to the sacral nerve. The sacral nerve response to applied electrical test stimulation can also be tested using the neurostimulation lead as the lead electrode is advanced. The combined probe and guide wire can be retracted from the lead body lumen when the testing is completed and the distal stimulation electrode(s) is optimally placed. The implantation procedure of the present invention employing the combined percutaneous medical probe and guide wire to form a percutaneous pathway for implanting a neurostimulation lead allows more rapid placement of the stimulation electrodes near the sacral nerves.

A similar procedure can be undertaken using the to implant leads and catheters or to guide tissue expanding introducers or dilators to other percutaneously accessed sites using the combined percutaneous medical probe and guide wire is to form a percutaneous. pathway. For example, the combined percutaneous medical probe and guide wire can be used to form a percutaneous pathway into the epidural space of the spinal column, into or adjacent to the stomach wall for the treatment of stomach disorders such as gastroparesis, into the large intestine for treatment of a paralyzed bowel condition or delayed bowel. Moreover, the combined percutaneous medical probe and guide wire can be used to form a percutaneous pathway through chest wall into the pericardial sac to provide a pathway to advance a cardiac pacing lead for treatment of bradycardia or a lead bearing a physiologic sensor to the pericardium. The lead may have a fixation mechanism for affixing pace/sense electrodes against the pericardium or into the myocardium.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Preferred embodiments of the invention are illustrated in the drawings, wherein like reference numerals refer to like elements in the various views, and wherein:

FIG. 1 is a plan view of a preferred embodiment of the combined percutaneous medical probe and guide wire of the present invention.

FIG. 2 is a side cross-section view of the guide wire construction taken along lines 2—2 of FIG. 1.

FIG. 3 is an end cross-section view of the guide wire construction taken along lines 3—3 of FIG. 1.

FIG. 4 is an end cross-section view of the guide wire construction taken along lines 4—4 of FIG. 1.

DESCRIPTION OF THE PREFERRED EMBODIMENTS

Figure 5:
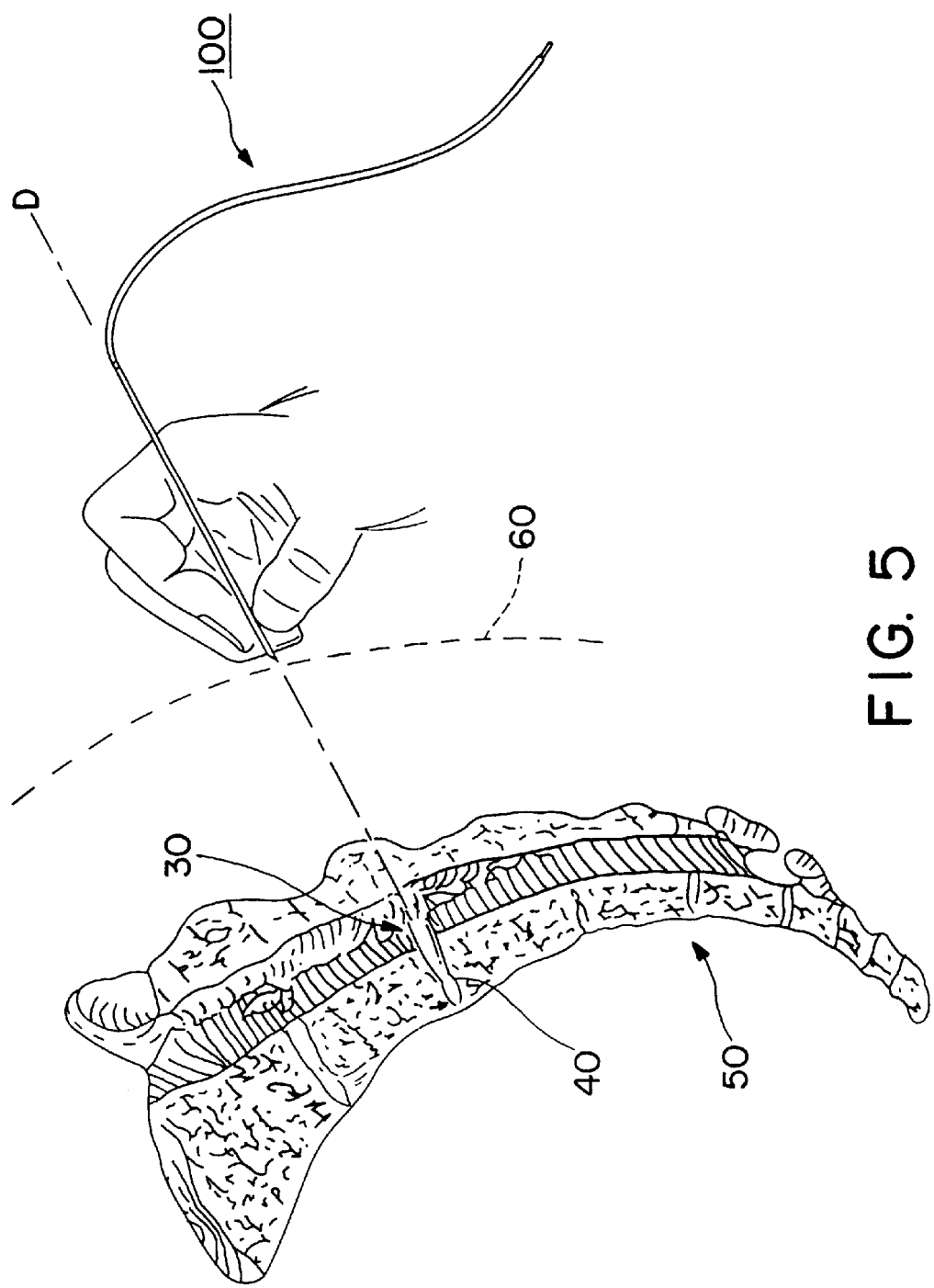
FIG. 5 is a schematic illustration of the percutaneous advancement of the medical probe of the combined percutaneous medical probe and guide wire to a percutaneously accessed site through a foramen of the sacrum.

A preferred embodiment of the combined probe and guide wire of the present invention is depicted in FIGS. 1–4, and a preferred use is depicted in FIGS. 5–9 optionally including the use of the dilator of FIGS. 10a–10c described further below. The combined probe and guide wire 100 comprises a stiff tissue penetrating probe 112 having a probe length between a probe proximal end 114 and a probe distal end 116 and a flexible guide wire body 120 having a guide wire length between a guide wire body proximal end 122 and a guide wire body distal end 124. The guide wire body distal end 124 is coupled to the probe proximal end 114.

The combined percutaneous medical probe and guide wire 100 is preferably covered along its length by an insulating coating 126 except for a distal exposed area providing an exposed electrode 128 for delivering stimulation to body tissue and an exposed electrical connector area of the guide wire body providing an exposed connector element 130. The internal structure of the probe 112 and guide wire body 120 conducts electrical signals between the distal exposed electrode 128 and the electrical connector element 130.

The flexible guide wire body 120 preferably comprises a coiled wire 132 extending between the guide wire body proximal end 122 and the guide wire body distal end 124 forming a coiled wire lumen 134 and an inextensible core wire 136. The core wire 138 extends through the coiled wire lumen 134 and is affixed to the coiled wire 132 at the guide wire body proximal end 122 and the guide wire body distal end 124 to inhibit stretching of the guide wire body 120. The core wire and the coiled wire can also conduct electrical signals generated by an electrical stimulator or electrical signals of the body from between the exposed electrode 128 and connector element 130.

Preferably, the tissue penetrating probe 112 has a probe lumen 140 extending distally from the probe proximal end 114 toward the probe distal end 116. The probe distal end 116 is preferably tapered to a sharpened tip, and the probe lumen 140 is filled at the tapered distal end 116. Preferably, the inextensible core wire 136 and wire coil 132 extend into the probe lumen 140 and are affixed to the tissue penetrating probe therein by welding and/or crimping to attach the guide wire body distal end 124 to the probe proximal end 114 as shown in FIG. 4. The core wire 136 can extend to the probe distal end 116 to fill the probe lumen at the tapered distal end 116.

The outer diameter of the combined percutaneous medical probe and guide wire i 100 is selected in relation to the through-lumen of a medical device, e.g., a lead an introducer, a dilator, a catheter or the like, so that the medical device can be advanced over the combined percutaneous medical probe and guide wire 100 after it is inserted transcutaneously as described further below to form a percutaneous pathway. The length of the probe 112 is selected to traverse the desired percutaneous pathway and is shorter than the length of the elongated medical device to be introduced therethrough. The length of the guide wire body 120 is selected in relation to the length of the medical device to enable grasping the guide wire body proximal end 122 upon advancement of the elongated medical device over the guide wire body 120. Then, the guide wire body 120 and elongated medical device overlying it can be axially aligned with the tissue penetrating probe 112 to enable advancement of the elongated medical device over the tissue penetrating probe 112 and through a percutaneous pathway.

The combined probe and guide wire 100 is therefore typically employed to form a percutaneous pathway to a percutaneously accessed site and to enable over-the-wire advancement of an elongated medical device having a device length and device through-lumen to the percutaneously accessed site or into an access pathway accessible from the percutaneously accessed site. The probe 112 is adapted to be manually grasped and advanced from the skin to the percutaneous access site to provide the percutaneous pathway to the percutaneously accessed site at the probe distal end.

One procedure for introducing a an elongated neurostimulation lead 10 over the combined percutaneous medical probe and guide wire 100 to locate the lead electrodes through a foramen 40 of the sacrum 50 at a percutaneously accessed site 30 adjacent to the sacral nerve (not shown) is depicted in FIGS. 5–9. The sacrum 50, generally speaking, is a large, triangular bone situated at the lower part of the vertebral column, and at the upper and back part of the pelvic cavity. The sacrum 50 is perforated by the anterior and posterior sacral foramina, e.g., foramen 40, that the sacral nerves pass through. The organs involved in bladder, bowel, and sexual function receive much of their control via the second, third, and fourth sacral nerves, commonly referred to as S2, S3 and S4 respectively. Electrical stimulation of these various nerves has been found to offer some control over these functions including control for bladder incontinence. Unlike other surgical procedures, sacral nerve stimulation using an imp lantable pulse generator is reversible by merely turning off the pulse generator.

Figure 10A:
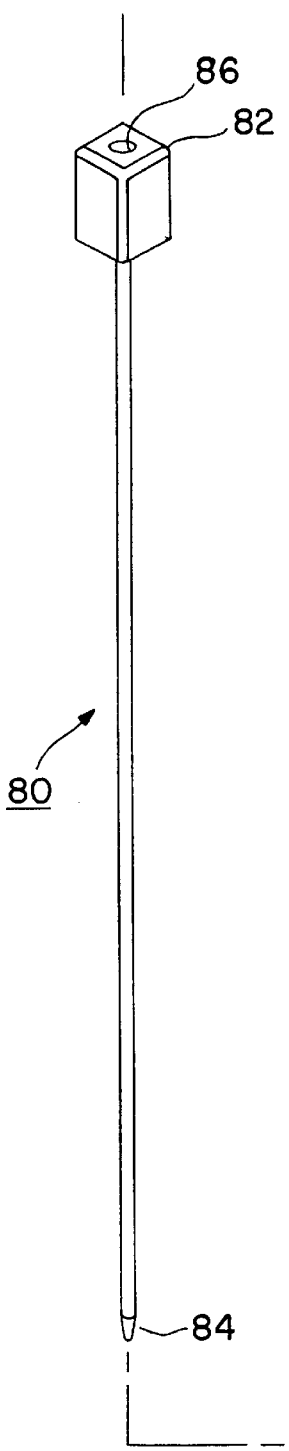
FIGS. 10a–10c illustrate a preferred dilator formed of the assembly of a dilator body and a dilator sheath usable in the procedure illustrated in FIGS. 5–9 to dilate the percutaneous pathway to facilitate introduction of the neurostimulation lead either over the combined percutaneous medical probe and guide wire of through the lumen of the dilator sheath.
Figure 10B:
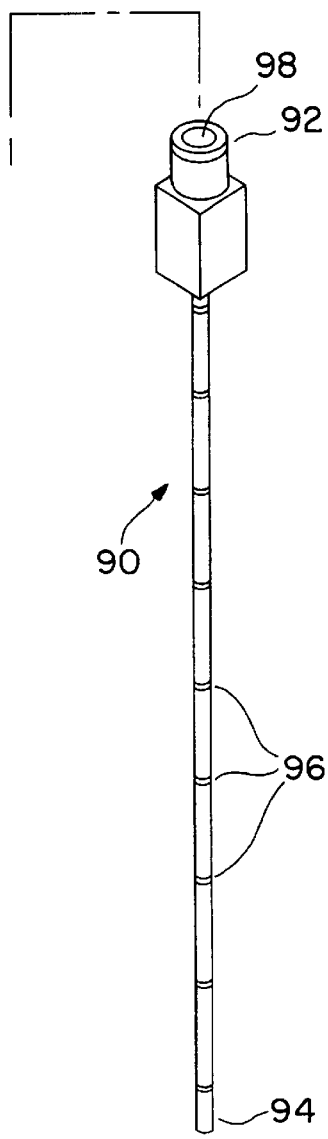
Figure 10C:
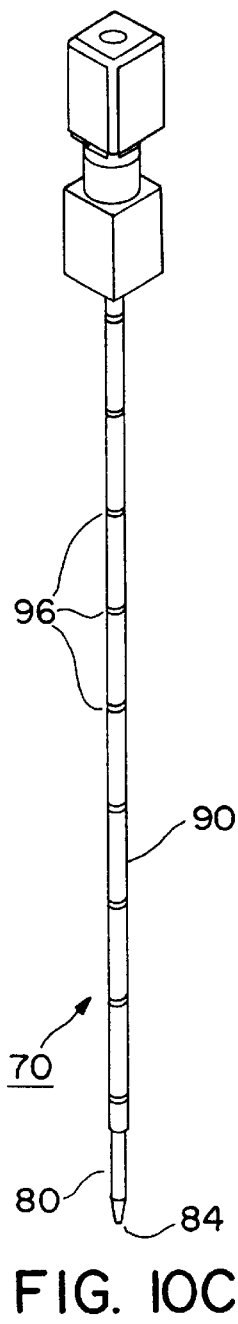

The minimally invasive method of the present invention for inserting an elongated medical device, e.g., lead 10 or the dilator 70 shown in FIGS. 10a–10c, having a device length and device through-lumen percutaneously to the percutaneously accessed site 30 commences in FIG. 5. In these illustrations, the elongated medical device comprises a neurostimulation lead 10 shown most particularly in FIG. 8. The neurostimulation lead 10 has a lead body 12 extending between a lead body proximal end 14 and a lead body distal end 16. A plurality of stimulation electrodes 18 are arrayed along a distal segment of the lead body 12, and a like plurality of in-line connector elements 20 are arrayed along a proximal segment of the lead body 14. The lead body 12 encloses a like plurality of conductors that are insulated electrically from one another and extend between each of the plurality of connector elements 20 and electrodes 18. A through-lumen extends within the lead body 12 from the lead body proximal end 14 to the lead body distal end 16. The lead body through-lumen diameter is sized to receive the combined probe and guide wire 100 for over-the-wire advancement.

In FIG. 5, the probe 112 is grasped, aimed in alignment with a predetermined direction D and advanced from the skin 60 to the percutaneously accessed site 30. The sharpened tip distal end 116 penetrates the surgically sterilized site on the skin or is advanced through a small skin incision toward the percutaneously accessed site 30 which is within or through the foramen 40 as the probe 112 is manually advanced in alignment with the direction D. Depth markings on the probe body and radiographic imaging can be employed to determine the depth of insertion and the location of the probe distal end 116.

Figure 6:
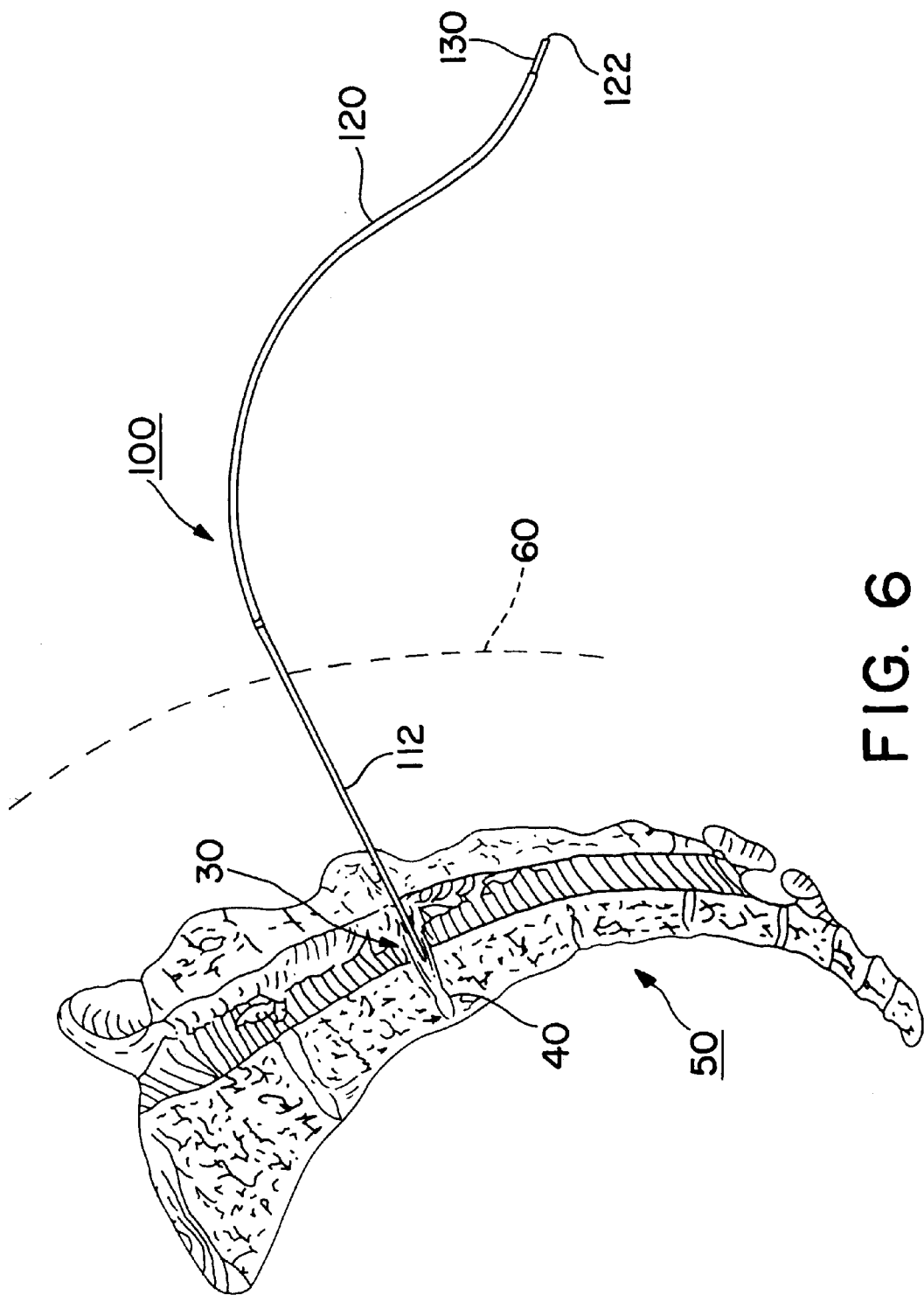
FIG. 6 is a schematic illustration of the percutaneous advancement of the medical probe of the combined percutaneous medical probe and guide wire to a percutaneously accessed site through a foramen of the sacrum.

The probe distal end 116 is shown fully advanced to the percutaneously accessed site 30 in FIG. 6. Test electrical stimulation can be applied at terminal 130 through the combined percutaneous medical probe and guide wire 100 to determine if stimulation applied through the probe distal end electrode 128 to the sacral nerve elicits a favorable response indicating optimal positioning. When testing is completed, the combined percutaneous medical probe and guide wire 100 depth provides the percutaneous pathway from the skin 60 to the percutaneously accessed site 30.

Figure 7:
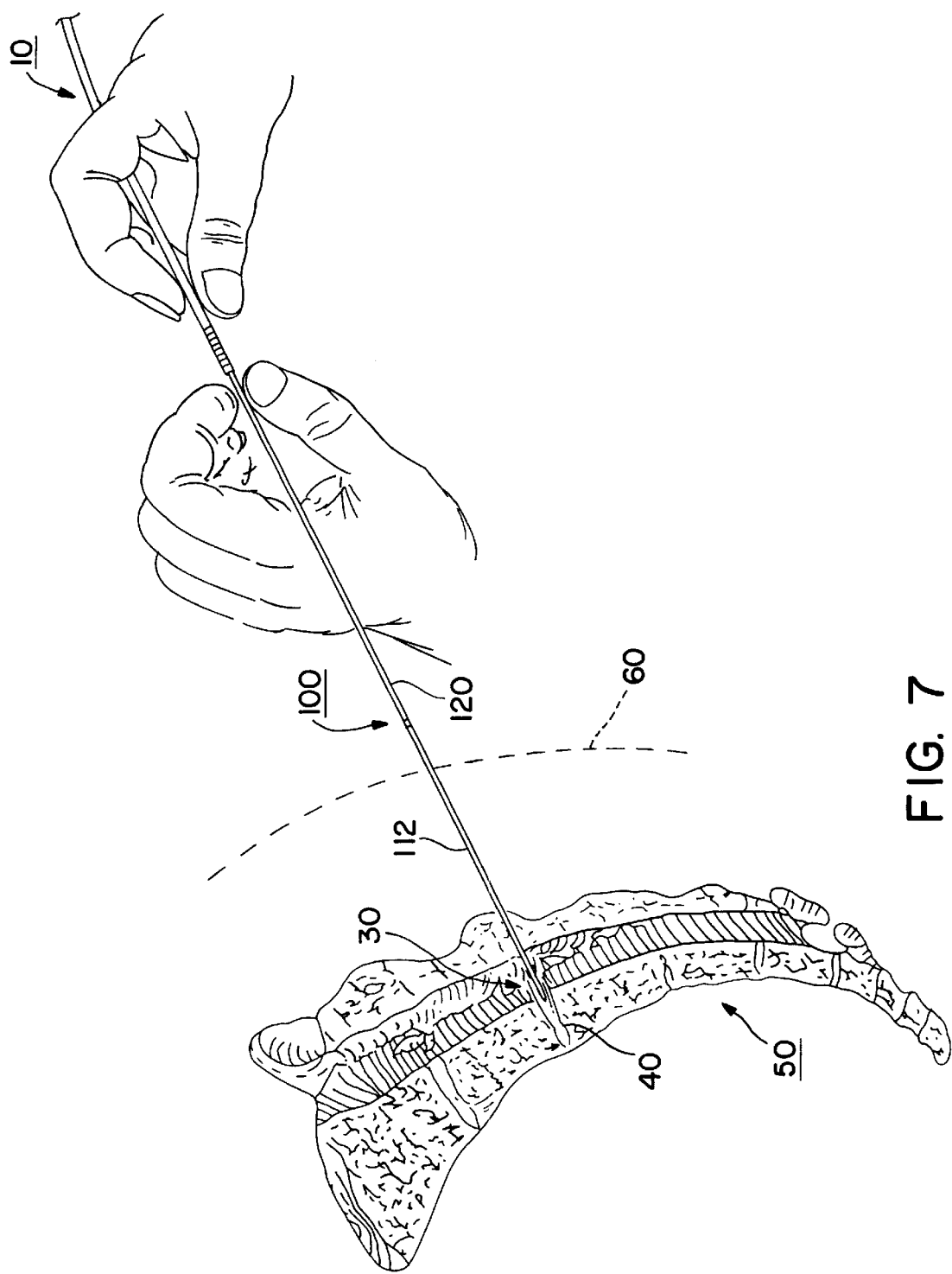
FIG. 7 is a schematic illustration of the straightening and insertion of the guide wire body proximal end into the through-lumen of an elongated neurostimulation lead.

In FIG. 7, the guide wire body 120 is straightened, and the guide wire body proximal end 122 is inserted into the through-lumen of the elongated neurostimulation lead 10. The elongated neurostimulation lead 10 is advanced over the over the guide wire body 120 as shown in FIG. 8 by grasping the guide wire body proximal end 122 upon advancement of the lead 10 over the guide wire body 120 to align the guide wire body 120 and elongated lead generally axially with the tissue penetrating probe 112 and in the direction D.

Figure 8:
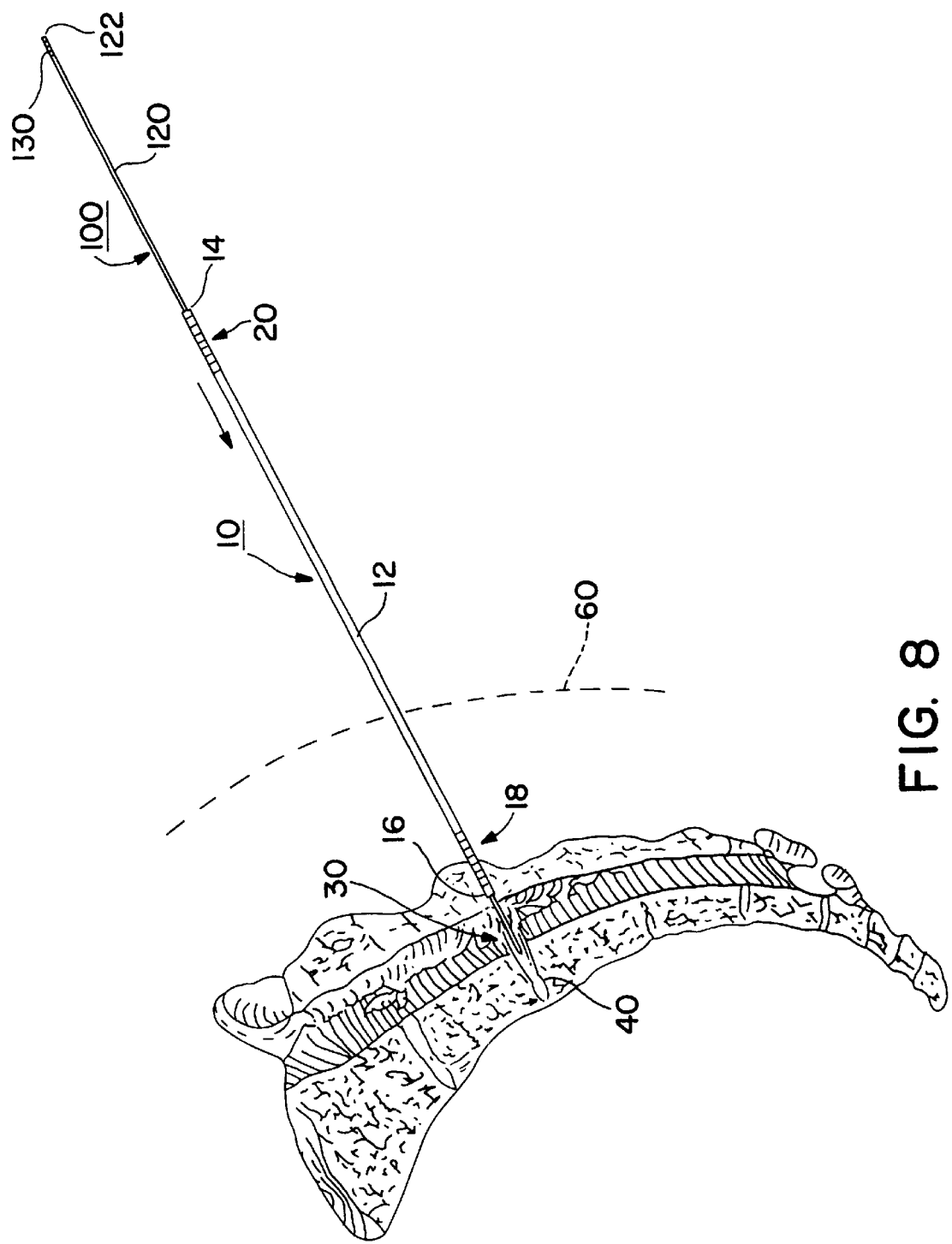
FIG. 8 is a schematic illustration of the advancement of the elongated neurostimulation lead over the combined percutaneous medical probe and guide wire to locate the lead electrodes at the percutaneously accessed site adjacent to the sacral nerve.
Figure 9:
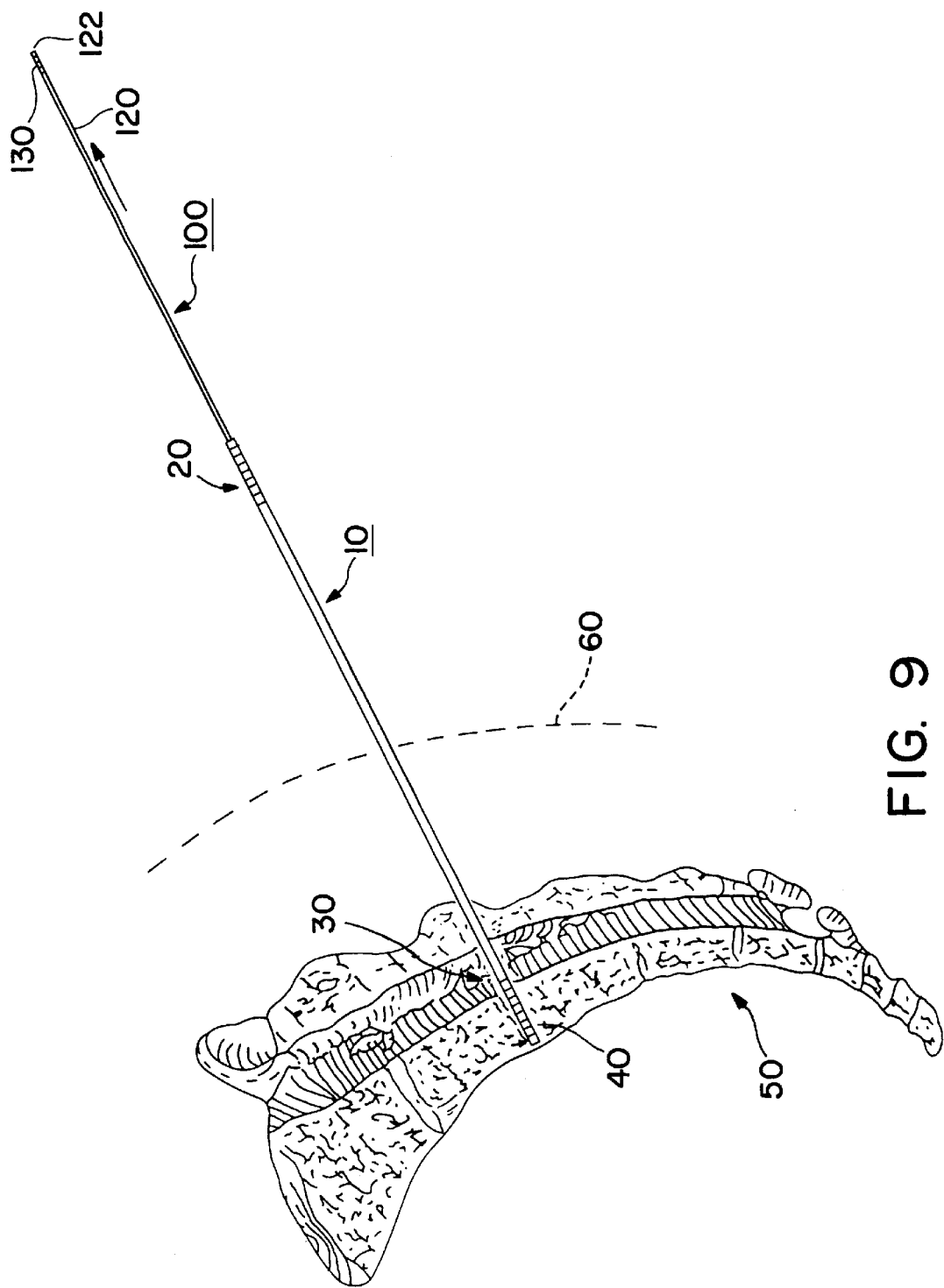
FIG. 9 is a schematic illustration of the withdrawal of the combined percutaneous medical probe and guide wire through the through-lumen of the elongated neurostimulation lead leaving the lead electrodes at the percutaneously accessed site adjacent to the sacral nerve.

The elongated lead is then advanced over the tissue penetrating probe 112 as shown in FIG. 8 until the lead electrodes 18 are located at the percutaneously accessed site 30 as shown in FIG. 9. The lead electrodes 18 can be moved back and forth to locate at least one or a pair of the electrodes in optimal location with respect to the sacral nerve to effect the desired response to test stimulation selectively applied through the electrodes. Then, the combined percutaneous medical probe and guide wire 100 is withdrawn through the through-lumen of the lead body 12 as shown in FIG. 9. The lead body 12 is fixed in place to prevent movement of the electrodes in a manner described in commonly assigned U.S. Pat. No. 5,484,445, for example. The lead connector elements 20 can then be coupled to an implantable neurostimulator in a manner known in the art.

The percutaneous pathway effected by the relatively short stiff probe 112 can be expanded by use of a dilator 70 formed of the assembly of a dilator body 80 and a dilator sheath 90 as shown in FIGS. 10a–10c. The dilator body 80 is preferably conductive, and the dilator sheath 90 is preferably non-conductive but may bear radiopaque and visually observable depth marks 96 along its length to facilitate radiographic imaging when it is extended into the paiient's body. The depth markings or marks 96 can be one centimeter or one-half centimeter bands or numerals or other indicia that indicate the depth of insertion to clinician from the exposed marking. The most distal mark is spaced from the distal tip of dilator sheath 90 to indicate a predetermined depth of the distal tip 84 of the dilator body 80 protruding distally during insertion as shown in FIG. 10c.

Thus, when assembled as shown in FIG. 10c, the dilator body distal end extends out of the dilator sheath distal end and is electrically exposed. Electrical stimulation of the sacral nerve to test placement can take place through the dilator body 80 while the dilator sheath 90 is in place The dilator body 80 has a dilator body diameter, a dilator body length extending between a dilator body proximal end 82 and a dilator body distal end 84, and a dilator body lumen 86 extending from the dilator proximal end to the dilator distal end. The dilator sheath 90 has a dilator sheath diameter, a dilator sheath length extending between a dilator sheath proximal end 92 and a dilator sheath distal end 94. A dilator sheath lumen 98 extends from the dilator sheath proximal end to the dilator sheath distal end, the dilator sheath lumen having a dilator sheath lumen diameter sized in operative relation to the dilator body diameter to selectively receive the dilator body therein to assemble the dilator body and dilator sheath as the dilator as shown in FIG. 10c. The dilator sheath lumen 98 is also sized in operative relation to the diameter of the neurostimulation lead body 12 so that the neurostimulation lead 10 can be advanced through the dilator sheath lumen 98 when the dilator body 80 is removed.

In this case, the dilator 70 is substituted for the lead 10 shown in FIG. 7, and the proximal end 122 of the combined percutaneous medical probe and guide wire 100 is inserted through the dilator body lumen 86. The dilator 70 is advanced over the combined percutaneous medical probe and guide wire 100 as shown in FIGS. 8 and 9 to dilate the percutaneous path. Then, either the entire dilator 70 or just the dilator body 80 can be withdrawn to enable the advancement of the lead 10 over the combined percutaneous medical probe and guide wire 100. Or, the dilator body 80 and the combined percutaneous medical probe and guide wire 100 can be withdrawn, and a neurostimulation lead that does not have a through-lumen can be advanced through the dilator sheath lumen 98.

Thus, it will be seen that the combined percutaneous medical probe and guide wire 100 can be used in a variety of other ways that will be apparent to those of skill in the art to facilitate advancement of implantable leads, catheters, dilators, introducers, cannula and tubes to various percutaneously accessed sites and in certain cases, from the percutaneously accessed site to a more remote site through an access pathway.

All patents and other publications referenced herein are incorporated herein by reference.

The true spirit and scope of the inventions of this specification are best defined by the appended claims, to be interpreted in light of the foregoing specification. Other apparatus that incorporate modifications or changes to that which has been described herein are equally included within the scope of the following claims and equivalents thereof. Therefore, to particularly point out and distinctly claim the subject matter regarded as the invention, the following claims conclude this specification.

We claim:

1. A combined percutaneous medical probe and guide wire employed to form a percutaneous pathway to a percutaneously accessed site and to enable over-the-wire advancement of an elongated medical device having a device length and device through-lumen to the percutaneously accessed site or into an access pathway accessible from the percutaneously accessed site comprising:

a stiff tissue penetrating probe having a probe length between a probe proximal end and a probe distal end, the probe adapted to be manually grasped and advanced from the skin to the percutaneous access site to provide the percutaneous pathway to the percutaneously accessed site at the probe distal end the probe length shorter than the device length; and a flexible guide wire body having a guide wire length between a guide wire body proximal end and a guide wire body distal end, the guide wire distal end coupled to the probe proximal end, the guide wire length sufficiently long to support the device length to enable its over-the-wire advancement over the guide wire body and probe.

2. The combined percutaneous medical probe and guide wire of claim 1, further comprising:

an insulating coating overlying the tissue penetrating probe except for a distal exposed electrode area and overlying the guide wire body except for an exposed electrical connector area of the guide wire body; and conductive means for conducting electrical signals between the distal exposed electrode area and the electrical connector area.

3. The combined percutaneous medical probe and guide wire of claim 2, wherein:

the flexible guide wire body comprises a coiled wire extending between the guide wire body proximal end and the guide wire body distal end forming a coiled wire lumen and an inextensible core wire extending through the coiled wire lumen and affixed to the coiled wire at the guide wire body proximal end and the guide wire body distal end to inhibit stretching of the guide wire body.

4. The combined percutaneous medical probe and guide wire of claim 2, wherein:

the tissue penetrating probe has a probe lumen extending distally from the probe proximal end;

the flexible guide wire body comprises a coiled wire extending between the guide wire body proximal end and the guide wire body distal end forming a coiled wire lumen and an inextensible core wire extending through the coiled wire lumen and affixed to the coiled wire at the guide wire body proximal end and extending into the probe lumen and affixed to the tissue penetrating probe to at least partially attach the guide wire body distal end to the probe proximal end and to inhibit stretching of the guide wire body.

5. The combined percutaneous medical probe and guide wire of claim 4, wherein the core wire extends distally through the probe lumen to the probe distal end.

6. The combined percutaneous medical probe and guide wire of claim 1, wherein:

the flexible guide wire body comprises a coiled wire extending between the guide wire body proximal end and the guide wire body distal end forming a coiled wire lumen and an inextensible core wire extending through the coiled wire lumen and affixed to the coiled wire at the guide wire body proximal end and the guide wire body distal end to inhibit stretching of the guide wire body.

7. The combined percutaneous medical probe and guide wire of claim 1, wherein:

the tissue penetrating probe has a probe lumen extending distally from the probe proximal end;

the flexible guide wire body comprises a coiled wire extending between the guide wire body proximal end and the guide wire body distal end forming a coiled wire lumen and an inextensible core wire extending through the coiled wire lumen and affixed to the coiled wire at the guide wire body proximal end and extending into the probe lumen and affixed to the tissue penetrating probe to at least partially attach the guide wire body distal end to the probe proximal end and to inhibit stretching of the guide wire body.

8. The combined percutaneous medical probe and guide wire of claim 7, wherein the core wire extends distally through the probe lumen to a distal core wire end at the probe distal end.

9. The combined percutaneous medical probe and guide wire of claim 8, wherein the core wire is electrically conductive and further comprising an electrical connector element formed along the flexible guide wire body electrically coupled to the core wire to enable delivery of electrical stimulation pulses through the core wire to the distal core wire end.

10. The combined percutaneous medical probe and guide wire of claim 1, wherein the guide wire length exceeds the device length to enable grasping the guide wire body proximal end upon advancement of the elongated medical device over the guide wire body to align the guide wire body and elongated medical device axially with the tissue penetrating probe to enable advancement of the elongated medical device over the tissue penetrating probe.

11. The combined percutaneous medical probe and guide wire of claim 1, wherein the elongated medical device comprises one of an electrical stimulation lead for stimulating a body organ, nerve or other tissue, a dilator for dilating tissue surrounding the combined percutaneous medical probe and guide wire, a catheter, an introducer, a cannula or a medical tube.

12. The combined percutaneous medical probe and guide wire of claim 1, wherein the elongated medical device comprises a sacral nerve stimulation lead, and the percutaneously accessed site comprises a site accessed through a foramen of the sacrum adjoining a sacral nerve.

13. The combined percutaneous medical probe and guide wire of claim 1, wherein the elongated medical device comprises a dilator comprising the assembly of:
   a dilator body having a dilator body diameter, a dilator body length extending between a dilator proximal end and a dilator distal end, and a dilator body lumen extending from the dilator proximal end to the dilator distal end and having a dilator body lumen diameter sized to receive the combined percutaneous medical probe and guide wire therein,
   a dilator sheath having a dilator sheath diameter, a dilator sheath length extending between a dilator sheath proximal end and a dilator sheath distal end, and a dilator sheath lumen extending from the dilator sheath proximal end to the dilator sheath distal end and having a dilator sheath lumen diameter sized in operative relation to the dilator body diameter to selectively receive the dilator body therein,
   whereby the dilator sheath and dilator body are adapted to be assembled with the dilator body received within the dilator sheath lumen, the dilator body is adapted to be inserted over the combined percutaneous medical probe and guide wire and to be advanced distally over the combined percutaneous medical probe and guide wire through the insertion path to dilate the insertion path to the dilator sheath diameter.

14. A minimally invasive method of inserting an elongated medical device having a device length and device through-lumen percutaneously to a percutaneously accessed site comprising the steps of:
   providing a combined percutaneous medical probe and guide wire comprising a stiff tissue penetrating probe having a probe length between a probe proximal end and a probe distal end, the probe length shorter than the elongated medical device length, and a flexible guide wire body having a guide wire length between a guide wire body proximal end and a guide wire body distal end, the guide wire distal end coupled to the probe proximal end, the guide wire length sufficiently long to support the elongated medical device to enable its over-the-wire advancement over the guide wire body and probe;
   manually grasping the probe and advancing the probe from the skin to the percutaneously accessed site to provide the percutaneous pathway to the percutaneously accessed site at the probe distal end;
   inserting the guide wire body proximal end into the through-lumen of the elongated medical device;
   advancing the elongated medical device over the guide wire body;
   grasping the guide wire body proximal end upon advancement of the elongated medical device over the guide wire body to align the guide wire body and elongated medical device generally axially with the tissue penetrating probe;
   advancing the elongated medical device over the tissue penetrating probe; and
   withdrawing the combined percutaneous medical probe and guide wire from the through-lumen of the medical device.

15. The method of claim 14, wherein the elongated medical device comprises one of an electrical stimulation lead for stimulating a body organ, nerve or other tissue, a dilator for dilating tissue surrounding the combined percutaneous medical probe and guide wire, a catheter, an introducer, a cannula or a medical tube.

16. The method of claim 14, wherein the elongated medical device comprises a sacral nerve stimulation lead, and the percutaneously accessed site comprises a site accessed through a foramen of the sacrum adjoining a sacral nerve.

17. A minimally invasive method of inserting an elongated a sacral nerve stimulation lead having a lead body length and lead body through-lumen percutaneously to a percutaneously accessed foramen of the sacrum adjoining a sacral nerve comprising the steps of:
   (a) providing a combined percutaneous medical probe and guide wire comprising a stiff tissue penetrating probe having a probe length between a probe proximal end and a probe distal end, the probe length shorter than the elongated medical device length, and a flexible guide wire body having a guide wire length between a guide wire body proximal end and a guide wire body distal end, the guide wire distal end coupled to the probe proximal end, the guide wire length sufficiently long to support the elongated medical device to enable its over-the-wire advancement over the guide wire body and probe;
   (b) manually grasping the probe and advancing,the probe from the skin to the percutaneously accessed site to provide the percutaneous pathway to the percutaneously accessed site adjoining a sacral nerve at the probe distal end;
   (c) inserting the guide wire body proximal end into the through-lumen of the elongated stimulation lead;
   (d) advancing the elongated stimulation lead over the guide wire body;
   (e) grasping the guide wire body proximal end upon advancement of the elongated stimulation lead over the guide wire body to align the guide wire body and elongated stimulation lead generally axially with the tissue penetrating probe;
   (f) advancing the elongated stimulation lead over the tissue penetrating probe to position lead stimulation electrodes in operative relation to the sacral nerve, (g) delivering test stimuli to the sacral nerve through the lead stimulation electrodes, and (h) withdrawing the combined percutaneous medical probe and guide wire from the through-lumen of the stimulation lead.

18. The method of claim 17 further comprising the steps of:

providing a dilator having a dilator through-lumen adapted to receive the combined percutaneous medical probe and guide wire; and before step (c), inserting the guide wire body proximal end into the through-lumen of the dilator; and expanding the percutaneous pathway by advancing the dilator over the combined percutaneous medical probe and guide wire.

19. A surgical instrumentation kit for minimally invasive implantation of a sacral stimulation lead through a foramen of the sacrum in a patient to electrically stimulate a sacral nerve, the sacral stimulation lead of the type having a lead body extending between a lead body proximal end and a lead body distal end, the lead body having a lead body diameter extending from the lead body proximal end and lead body distal end, the lead body further enclosing at least one electrical conductor extending between at least one proximally located electrical connector adapted to be coupled to an electrical stimulation pulse generator and at least one distally located stimulation electrode adapted to apply electrical stimulation to a sacral nerve, the kit comprising:

a combined percutaneous medical probe and guide wire comprising a stiff tissue penetrating probe having a probe length between a probe proximal end and a probe distal end, the probe length shorter than the lead body length, and a flexible guide wire body having a guide wire length between a guide wire body proximal end and a guide wire body distal end, the guide wire distal end coupled to the probe proximal end, the guide wire length sufficiently long to support the elongated lead body to enable its over-the-wire advancement over the guide wire body and probe, the probe distal end capable of penetrating body tissue, the probe adapted to be grasped by a medical clinician with the probe distal end directed toward and inserted through an entry point of the skin or a skin incision posterior to the sacrum and guided along an insertion path into a foramen to locate at least a distal portion of the probe extending alongside a sacral nerve and a proximal portion of the probe extending from the entry point away from the patient's skin; and a dilator body having a dilator body diameter, a dilator body length extending between a dilator proximal end and a dilator distal end, and a dilator body lumen extending from the dilator proximal end to the dilator distal end and having a dilator body lumen diameter sized to receive the combined percutaneous medical probe and guide wire therein, a dilator sheath having a dilator sheath diameter, a dilator sheath length extending between a dilator sheath proximal end and a dilator sheath distal end, and a dilator sheath lumen extending from the dilator sheath proximal end to the dilator sheath distal end and having a dilator sheath lumen diameter sized in operative relation to the dilator body diameter to selectively receive the dilator body therein, whereby the dilator sheath and dilator body are adapted to be assembled with the dilator body received within the dilator sheath lumen, the dilator body is adapted to be inserted over the combined percutaneous medical probe and guide wire and to be advanced distally over the combined percutaneous medical probe and guide wire through the insertion path to dilate the insertion path to the dilator sheath diameter.

20. The surgical instrumentation kit of claim 19, wherein the combined percutaneous medical probe and guide wire is adapted to be withdrawn through the dilator body lumen, the dilator body is adapted to be withdrawn through the dilator sheath lumen.

* * * * *